(12) United States Patent
Mullaney

(10) Patent No.: US 11,364,054 B2
(45) Date of Patent: Jun. 21, 2022

(54) ADJUSTABLE STRUT ASSEMBLIES FOR EXTERNAL FIXATION SYSTEMS

(71) Applicant: AMDT HOLDINGS, INC., Collierville, TN (US)

(72) Inventor: Michael W. Mullaney, Naples, FL (US)

(73) Assignee: AMDT HOLDINGS, INC., Collierville, TN (US)

( * ) Notice: Subject to any disclaimer, the term of this patent is extended or adjusted under 35 U.S.C. 154(b) by 0 days.

(21) Appl. No.: 17/185,460

(22) Filed: Feb. 25, 2021

(65) Prior Publication Data
US 2021/0244442 A1 Aug. 12, 2021

Related U.S. Application Data

(63) Continuation of application No. PCT/US2019/048931, filed on Aug. 29, 2019.

(60) Provisional application No. 62/724,462, filed on Aug. 29, 2018.

(51) Int. Cl.
*A61B 17/62* (2006.01)
*A61B 17/64* (2006.01)

(52) U.S. Cl.
CPC .......... *A61B 17/6475* (2013.01); *A61B 17/62* (2013.01)

(58) Field of Classification Search
CPC .......... A61B 17/62; A61B 17/64–6491; A61B 17/66
See application file for complete search history.

(56) References Cited

U.S. PATENT DOCUMENTS 5,314,426 A 5/1994 Pohl et al.
5,702,196 A 12/1997 Petercsak
(Continued)

FOREIGN PATENT DOCUMENTS

WO 2017139517 8/2017

OTHER PUBLICATIONS

International Search Report and Written Opinion of the International Searching Authority for International Application No. PCT/US2019/048931 dated Oct. 29, 2019.

*Primary Examiner* — Eduardo C Robert
*Assistant Examiner* — Michelle C Eckman
(74) *Attorney, Agent, or Firm* — Heslin Rothenberg Farley & Mesiti PC; John W. Boger, Esq.; Kristian E. Ziegler, Esq.

(57) ABSTRACT

Length-adjustable strut assemblies for external fixation systems, and corresponding external fixation systems, are disclosed. The strut assemblies include an elongate first and second end members, an elongate intermediate member, and first and second adjustment mechanisms. The intermediate member comprises a threaded rod fixedly coupled within an axial cavity thereof, and is rotatably fixed and axially translatably within an axial cavity of the first end member. An end portion of the second end member is received within the axial cavity of the intermediate member, and the second end member comprises an axial cavity threadably coupled with the threaded rod. The first adjustment mechanism is configured to selectively axially fix the intermediate member relative to the first end member. The second adjustment mechanism is configured to selectively rotate the second end member with respect to the threaded rod to axially translate the second end member relative to the intermediate member.

40 Claims, 17 Drawing Sheets

(56) References Cited

U.S. PATENT DOCUMENTS

| | | | |
|---|---|---|---|
| 2010/0312243 A1* | 12/2010 | Ross | A61B 17/645 |
| | | | 606/56 |
| 2010/0331840 A1* | 12/2010 | Ross | A61B 17/62 |
| | | | 606/54 |
| 2011/0208187 A1 | 8/2011 | Wong | |
| 2013/0296857 A1* | 11/2013 | Barnett | A61B 17/6416 |
| | | | 606/57 |
| 2017/0354439 A1* | 12/2017 | Mannanal | A61B 17/66 |

* cited by examiner

ADJUSTABLE STRUT ASSEMBLIES FOR EXTERNAL FIXATION SYSTEMS

CROSS REFERENCE TO RELATED APPLICATIONS

This application claims priority benefit from International Application No. PCT/US2019/048931 filed on Aug. 29, 2019, which claimed priority from U.S. Provisional Application No. 62/724,462 filed Aug. 29, 2018, each of which is incorporated herein by reference in its entirety.

FIELD OF THE DISCLOSURE

The present disclosure is generally directed to struts for external fixation systems and related methods. More particularly, the present disclosure is directed to adjustable strut assemblies for external fixation systems and related methods that provide for relatively quick length adjustment over a relatively large length adjustment range.

BACKGROUND

External fixation devices have been used to treat bone and tissue conditions by positioning and orienting bone or tissue segments in desired relative positions and orientations, and adjusting their relative positions and orientations, based on particular clinical needs. One form of external fixation devices is a hexapod fixation device. Hexapod devices, or more formally called Stewart platforms, include six degree of freedom (6DOF) parallel manipulators or struts. Generally, these devices have the ability to manipulate an article of interest relative to a base in all three orthogonal axis translations (X, Y, Z position) and all rotations about those three orthogonal axes (roll, pitch, yaw pose). Other types of external fixation devices utilize less than six struts or more than six struts.

External fixation systems also typically include a pair of platforms or "rings" that serve as bone fixation platforms. The platforms are typically connected with six struts that extend between the platforms. The struts and platforms are commonly connected via spherical or cardan joints that allow three rotations about three orthogonal axes. While some of these struts allow for length adjustment, their minimum and/or maximum lengths may not meet the needs of a particular clinical situation. For example, minimizing the distance between the platforms to a distance less than that afforded by a particular strut requires the use of shorter struts—which naturally limits the adjustable range (i.e., the maximum length) of the struts.

As a result, current hexapod bone fixation systems utilize a collection of struts of differing lengths (or differing length ranges) which provide "short" struts for use when the platforms need to be close together and "long" struts for use when the platforms need to be further apart. In many instances these struts must be progressively or regressively swapped for the next length strut during a bone or tissue correction process, which is both a time consuming and costly process given that the strut being replaced cannot be re-used. Further complicating such systems is that some situations require a variety of differing strut lengths. For example, a variety of differing strut lengths is commonly required when extreme initial angulations or rotations are present. The selection process of the correct combination of differing strut lengths in such a situation is a time consuming process that is typically carried out by trial and error in an operating room. Such systems and situations thereby also require an excessive amount of inventory, which is also costly and often confusing to properly utilize.

Physically changing struts, aside from being a nuisance, also limits the available dynamic range of the system when attempting to reduce a deformity in an acute fashion. In this situation, struts are usually not added until such an acute correction is accomplished leaving the reduction to be held by operation room staff while additional members of the operation room staff pick and choose which struts will fit between the platforms at the prescribed locations. This process is time consuming and requires a large inventory.

Current hexapod fixation systems also typically utilize connections between the platforms and struts that require the use of one or more fasteners that need to be tightened at the time of application. As such, connecting six struts at both ends to the platforms (i.e., twelve connections), sometimes in a trial and error fashion, is a difficult and time consuming task. Complicating matters is the fact that many current hexapod fixation systems utilize loose fasteners which must be applied using instruments. These fasteners and instruments add to the collection of parts and materials which must be kept track of in an operating room setting while the fixation system is employed, such as while a reduction is trying to be maintained.

Accordingly, strut assemblies, external fixation systems including such strut assemblies and related methods that provide increased length adjustment ranges and can be adjusted relatively quickly and easily, particularly while remaining coupled to the platforms/user, are desirable.

SUMMARY OF THE INVENTION

In one aspect, the present disclosure provides a strut assembly for an external bone and/or tissue fixation system. The strut assembly includes an elongate tubular first end member, an elongate tubular intermediate member rotationally fixed and axially translatably within an axial cavity of the first end member and extending therefrom from a first end portion thereof, and an elongate tubular second end member received within an axial cavity of the intermediate member and extending therefrom from a second end portion thereof. The intermediate strut body is rotationally fixed and axially translatably coupled within the first end member and extends axially therefrom from a first end portion of the first end member. The strut assembly further includes a first adjustment mechanism provided at the first free end portion of the first end member that is configured to selectively allow the intermediate member to freely axially translate within the first end member and to selectively axially fix the first end member and the intermediate member. The strut assembly further comprises a threaded rod fixed within an axial internal cavity of the intermediate member. An axial cavity of the second member is threadably coupled with the threaded rod within the cavity of the intermediate member and extends axially therefrom from a second end portion of the intermediate member. The strut assembly further includes a second adjustment mechanism provided at the second free end portion of the intermediate member that is configured to selectively rotate the second end member with respect to the intermediate member and the threaded rod to axially translate the second end member relative to the intermediate member.

In another aspect, the present disclosure provides a strut assembly for an external fixation system comprising an elongate first end member, an elongate intermediate member, an elongate second end member, a first adjustment mechanism and a second adjustment mechanism. The first end member comprises a first end portion, a second end portion, and a first axial cavity extending from the second end portion. The intermediate member comprises a third end portion, a fourth end portion, a second axial cavity extending from the third end portion, and a threaded rod fixedly coupled within the second axial cavity. The intermediate member is rotatably fixed and axially translatably within the first axial cavity of the first end member and extends therefrom through the second end portion. The second end member comprises a fifth end portion, a sixth end portion, and a third axial cavity extending from the fifth end portion. At least the fifth end portion of the second end member is received within the second axial cavity of the intermediate member, and the third axial cavity is threadably coupled with the threaded rod of the intermediate member. The second end member extends from the second axial cavity through the fourth end portion. The first adjustment mechanism is positioned at the second end portion of the first end member and is configured to selectively allow the intermediate member to freely axially translate within the first axial cavity and to selectively axially fix the intermediate member relative to the first end member. The second adjustment mechanism is positioned at the fourth free end portion of the intermediate member and is configured to selectively rotate the second end member with respect to the intermediate member and the threaded rod to axially translate the second end member relative to the intermediate member.

In some embodiments, the first end portion of the first end member includes a first joint configured to couple to a first external fixation platform. In some embodiments, the sixth end portion of the second end member includes a second joint configured to couple to a second external fixation platform.

In some embodiments, a body portion of the first end member includes an axial-extending slot, and the intermediate member is rotatably fixed and axially translatably within the first axial cavity of the first end member via a radially extending first pin that is coupled to the intermediate member and is received within the slot of the first end member. In some such embodiments, the first pin is coupled to the third end portion of the intermediate member. In some such embodiments, the first pin is further coupled to the threaded rod to rotatably and axially fixedly couple the threaded rod and the intermediate member. In some such embodiments, the first pin is coupled to an end portion of the threaded rod.

In some embodiments, at least the fifth end portion of the second end member received within the second axial cavity of the intermediate member is positioned radially between the threaded rod and a body portion of the intermediate member. In some embodiments, the third axial cavity of the intermediate member comprises internal threads and the threaded rod comprises external threads threadably coupled with the internal threads of the third axial cavity.

In some such embodiments, the second end portion of the first end member comprises external threads, the first adjustment mechanism comprises an internally threaded first collar member threadably coupled with the external threads of the second end portion, and rotation of the first collar member about the second end portion axially translates the first collar along the second end portion. In some such embodiments, a clamping portion of the first collar member is positioned axially past the second end portion of the first end member and includes a tapered bearing surface, and the first adjustment mechanism further comprises friction member positioned radially between the exterior surface of a body portion of the intermediate member and the bearing surface. In some such embodiments, axial translation of the first collar along the second end portion towards the first end portion forces the friction member radially against the exterior surface of a body portion of the intermediate member via the bearing surface to selectively axially fix the intermediate member relative to the first end member. In some embodiments, the bearing surface comprises a surface that is angled towards the exterior surface of the body portion of the intermediate member as it extends axially away from the second end portion. In some embodiments, the friction member comprises a deformable ring member. In some such embodiments, the deformable ring member comprises a segmented ring or a split ring. In some such embodiments, the exterior surface of the body portion of the intermediate member comprises a friction-enhancing surface texture.

In some such embodiments, the second adjustment mechanism comprises a second collar member axially fixed and rotatably coupled to the fourth end portion of the intermediate member. In some such embodiments, a body portion of second end member includes an axial-extending slot, and the second collar member is rotatably fixed to the second end member via a radially extending second pin that is coupled to the second collar member and is received within the slot of the second end member such that rotation of the second collar member about the fourth end portion axially translates the second end member relative to the intermediate member.

In another aspect, the present disclosure provides an external bone and/or tissue fixation system comprising a first platform, a second platform, and a plurality of struts extending between the first and second platforms, at least one of the plurality of struts comprises a strut assembly disclosed herein.

In some embodiments, a plurality of the plurality of struts comprise a strut assembly disclosed herein. In some embodiments, each of the plurality of struts comprises a strut assembly disclosed herein. In some embodiments, the plurality of struts comprises six struts. In some embodiments, the first platform is configured to couple with a first bone and/or tissue, and the second platform is configured to couple with a second bone and/or tissue of a patient.

In some embodiments, the first end portion of the first end member includes a first joint configured to couple to a first external fixation platform. In some embodiments, sixth end portion of the second end member includes a second joint configured to couple to a second external fixation platform. In some embodiments, a body portion of the first end member includes an axial-extending slot, and the intermediate member is rotatably fixed and axially translatably within the first axial cavity of the first end member via a radially extending first pin that is coupled to the intermediate member and is received within the slot of the first end member. In some such embodiments, the first pin is coupled to the third end portion of the intermediate member. In some other such embodiments, the first pin is further coupled to the threaded rod to rotatably and axially fixedly couple the threaded rod and the intermediate member. In some embodiments, the first pin is coupled to an end portion of the threaded rod.

In some embodiments, at least the fifth end portion of the second end member received within the second axial cavity of the intermediate member is positioned radially between the threaded rod and a body portion of the intermediate member. In some such embodiments, the third axial cavity of the intermediate member comprises internal threads and the threaded rod comprises external threads threadably coupled with the internal threads of the third axial cavity.

In some such embodiments, the second end portion of the first end member comprises external threads, the first adjustment mechanism comprises an internally threaded first collar member threadably coupled with the external threads of the second end portion, and rotation of the first collar member about the second end portion axially translates the first collar along the second end portion. In some such embodiments, a clamping portion of the first collar member is positioned axially past the second end portion of the first end member and includes a tapered bearing surface, and the first adjustment mechanism further comprises friction member positioned radially between the exterior surface of a body portion of the intermediate member and the bearing surface. In some such embodiments, axial translation of the first collar along the second end portion towards the first end portion forces the friction member radially against the exterior surface of a body portion of the intermediate member via the bearing surface to selectively axially fix the intermediate member relative to the first end member. In some such embodiments, the bearing surface comprises a surface that is angled towards the exterior surface of the body portion of the intermediate member as it extends axially away from the second end portion. In some such embodiments, the friction member comprises a deformable ring member. In some such embodiments, the deformable ring member comprises a segmented ring or a split ring. In some embodiments, the exterior surface of the body portion of the intermediate member comprises a friction-enhancing surface texture.

In some embodiments, the second adjustment mechanism comprises a second collar member axially fixed and rotatably coupled to the fourth end portion of the intermediate member. In some such embodiments, a body portion of second end member includes an axial-extending slot, and the second collar member is rotatably fixed to the second end member via a radially extending second pin that is coupled to the second collar member and is received within the slot of the second end member such that rotation of the second collar member about the fourth end portion axially translates the second end member relative to the intermediate member.

These and other objects, features and advantages of this disclosure will become apparent from the following detailed description of the various aspects of the disclosure taken in conjunction with the accompanying drawings.

BRIEF DESCRIPTION OF THE DRAWINGS

For the purposes of illustrating the external bone fixation systems and related methods described herein there is shown illustrative embodiments. These illustrative embodiments are in no way limiting in terms of the precise arrangement and operation of the disclosed external fixation systems and other similar embodiments are envisioned.

DETAILED DESCRIPTION

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

The present disclosure provides for length adjustable strut assemblies 10 for external fixation systems that include a large adjustment range and can be manually adjusted quickly and easily, even while remaining coupled to platforms/baseplates (and thereby the user), as shown in FIGS. 1-11. The present disclosure thereby also provides external fixation/parallel manipulator systems 100 (e.g., six degree of freedom (6DOF) fixation systems), and related fixation methods, that incorporate one or more of the strut assemblies 10, as shown in FIGS. 12-19. For example, in some embodiments, the external fixation system 100 may include at least one strut assembly 10. In some other embodiments, the external fixation system 100 may include a plurality of the strut assemblies 10. In some embodiments, each strut of the external fixation system 100 may comprise the strut assembly 10. In some embodiments, the external fixation systems 100 are bone and/or tissue fixation systems.

Via the strut assemblies 10, the external fixation system 100 can thereby include the desirable stability and mobility characteristics of a traditional parallel manipulator systems, but without the time consuming strut-length choices, strut-length limitations and strut disassembly and assembly difficulties. The struts assembly 10, and thereby a fixation system 100 including one or more struts assembly 10, includes a relatively large dynamic/adjustment range (including a gross adjustment range and a fine adjustment range) such that replacement of the one or more struts assemblies 10 during a reduction/distraction process is eliminated (or at least less likely). In some embodiments, struts assembly 10, and thereby a fixation system 100 including one or more of the struts assemblies 10, are particularly advantageous for the repair of fractures or deformities, such as fractures of or deformities in relatively long bones.

Figure 1:
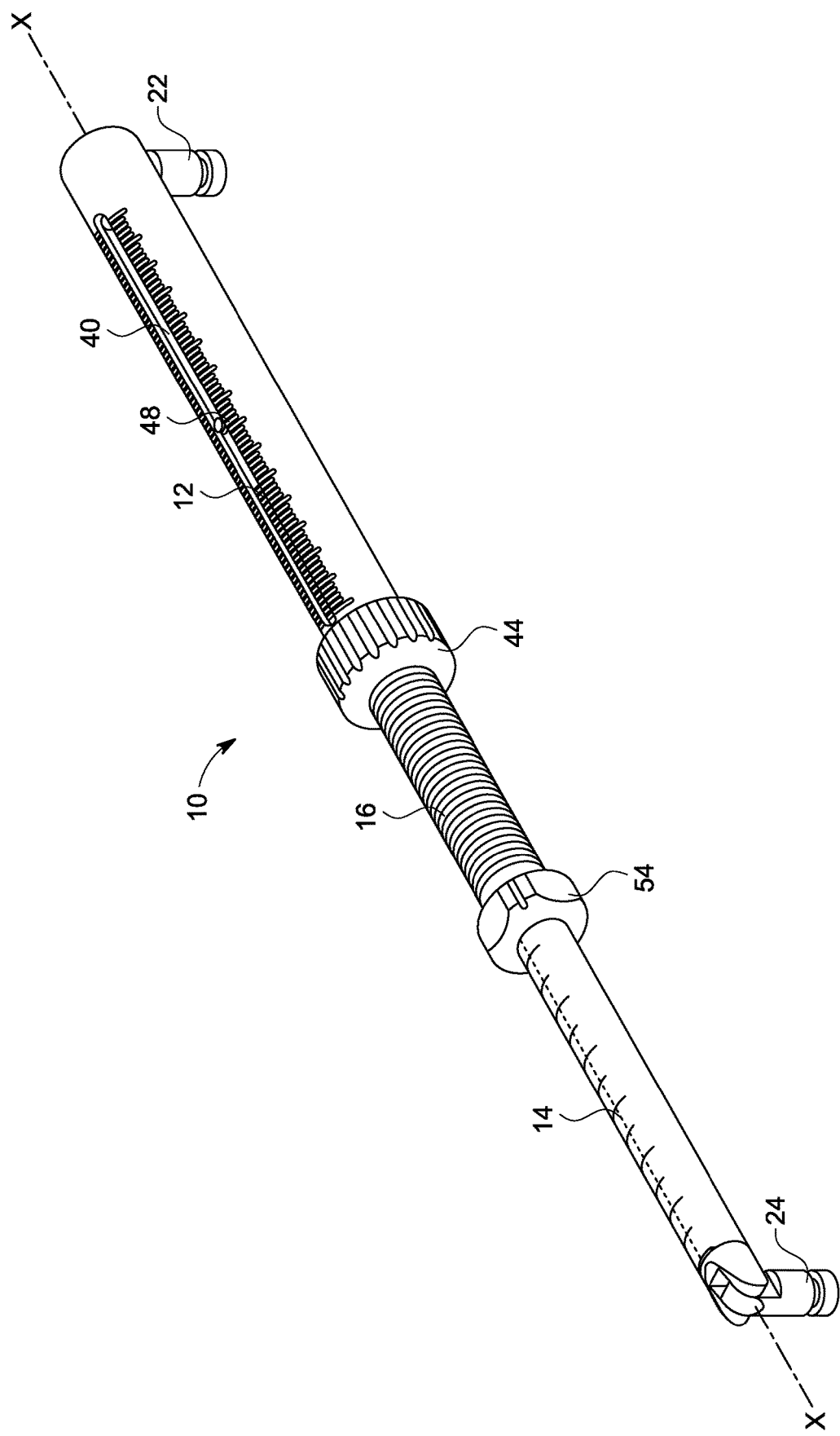
FIG. 1 illustrates a front elevational perspective view of an exemplary adjustable strut assembly, according to the present disclosure.
Figure 2:
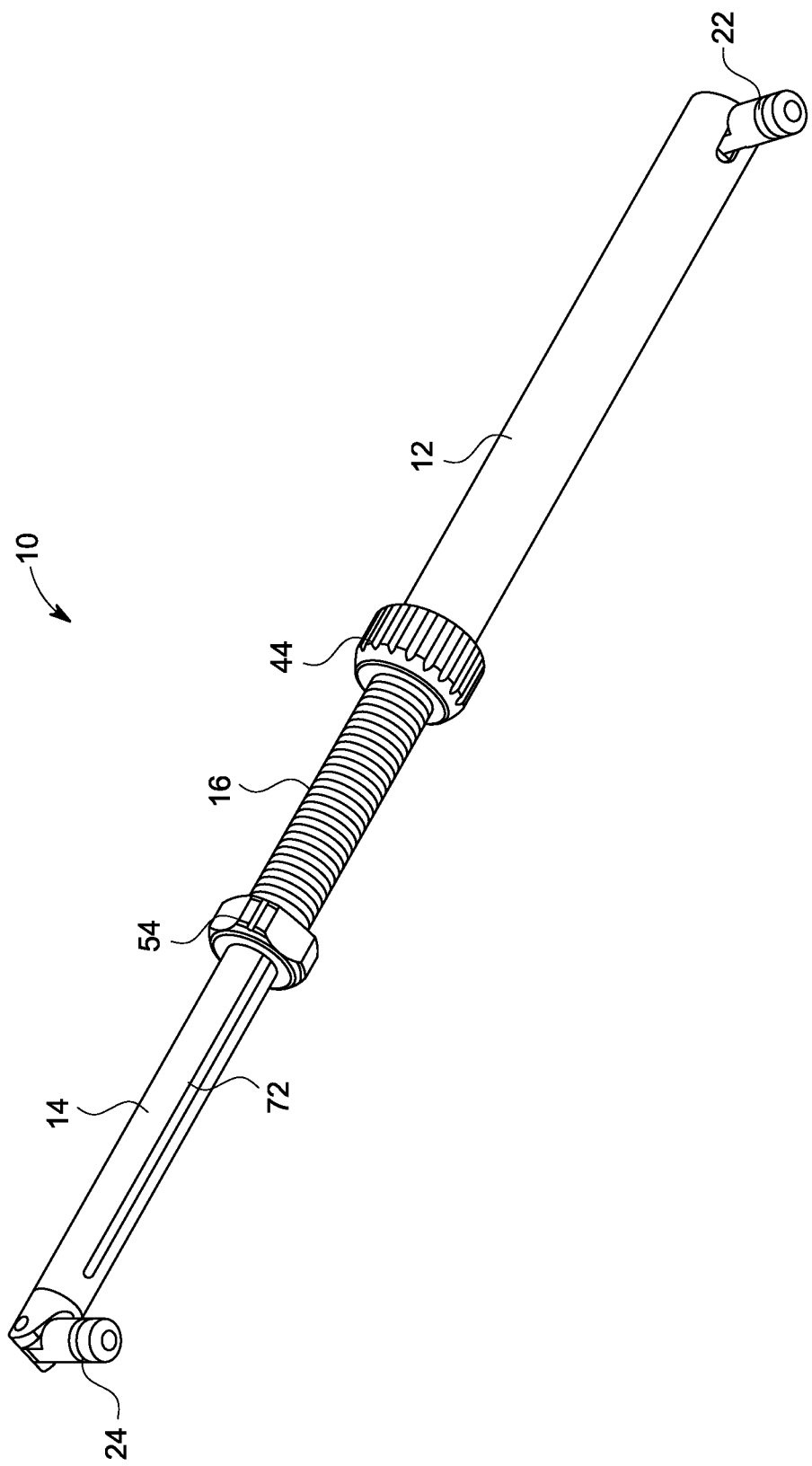
FIG. 2 illustrates a back elevational perspective view of the exemplary adjustable strut assembly of FIG. 1, according to the present disclosure.
Figure 3:
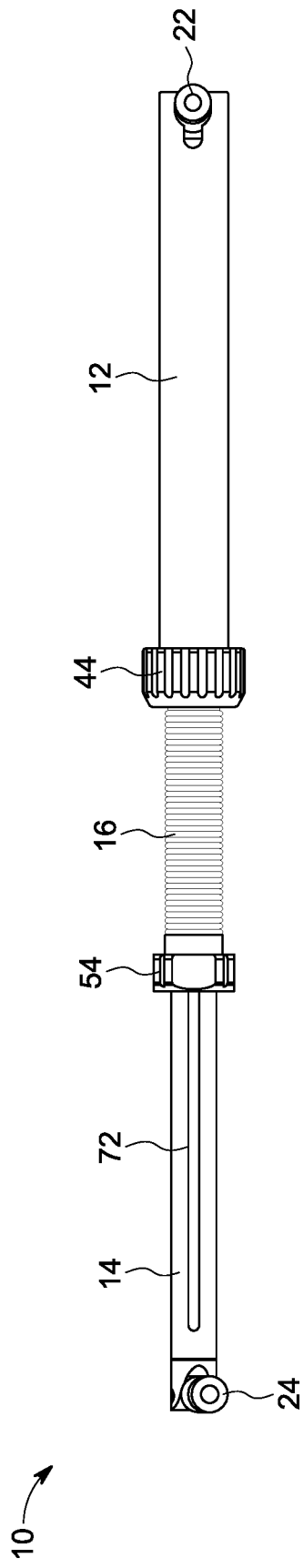
FIG. 3 illustrates a back view of the exemplary adjustable strut assembly of FIG. 1, according to the present disclosure.
Figure 4:
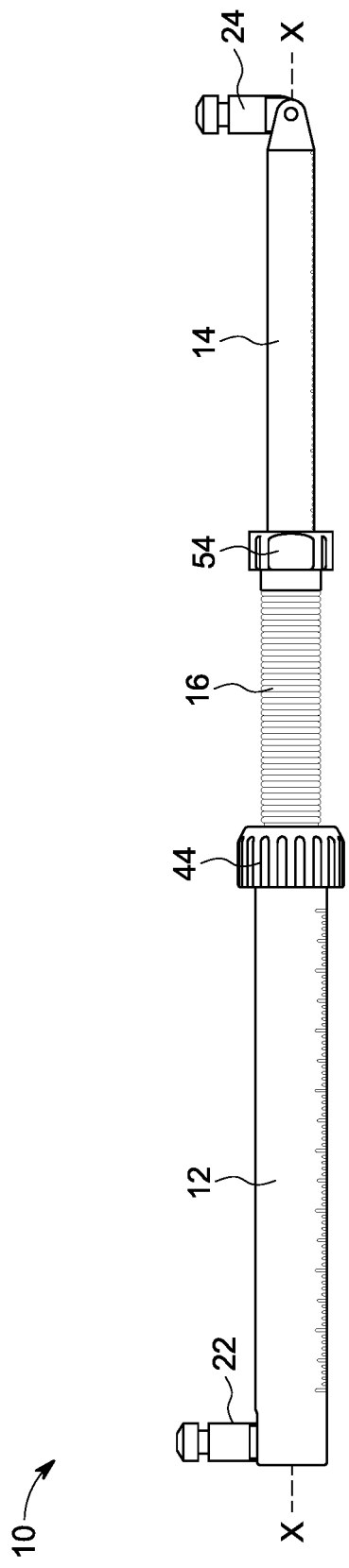
FIG. 4 illustrates a side view of the exemplary adjustable strut assembly of FIG. 1, according to the present disclosure.
Figure 5:
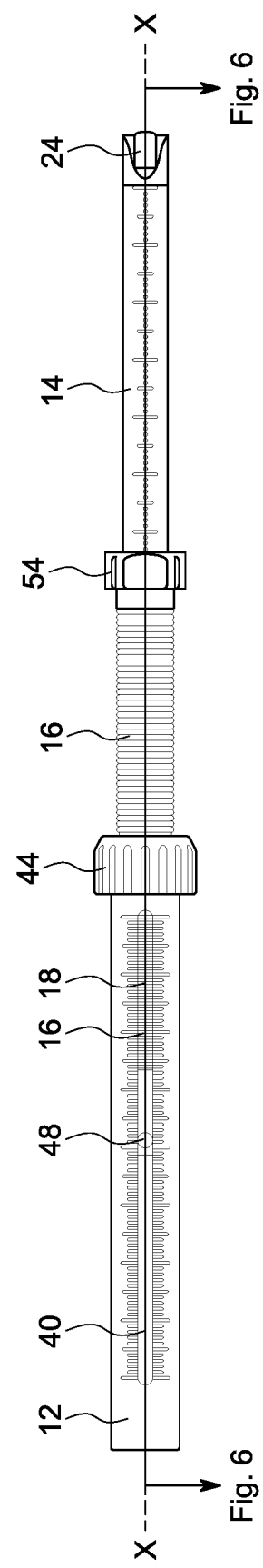
FIG. 5 illustrates a front view of the exemplary adjustable strut assembly of FIG. 1, according to the present disclosure.

In some embodiments, the strut assemblies 10 are each formed of an assembly of an axially-elongated tubular first end member or strut body 12, a second axially-elongated tubular first end member or strut body 14, and an axially-elongated tubular intermediate member strut body 16 that couples and extends between the first end member 12 and the second end member 14, as shown in FIGS. 1-11. As explained further below, the strut assemblies 10 also include a threaded rod 18 fixed within the intermediate member 16 and threadably coupled within an axially-extending cavity of the second end member 14. The intermediate member 16 is also axially translatably coupled within an axially-extending cavity of the first end strut body 12. The strut assemblies 10 may include or define a longitudinal axis X-X, and the total length thereof along the axis X-X is adjustable (both grossly and finely adjustable), as shown in FIGS. 1, 4 and 5. The axial ends of the strut assembly formed by the first and second end members 12, 14 may include first and second joints or connection mechanisms 22, 24, respectively, as shown in FIGS. 1-6, 10 and 11. The first and second joints 22, 24 are configured to couple to/with one of first and second platforms or baseplates 120, 130 of an external fixation system 100, as shown in FIGS. 12-19.

As shown in FIGS. 12-19, the first joint 22 can be coupled to a first platform 120, and the second joint 24 can be coupled to a second platform 130. In this way, the relative axial position of the intermediate member 16 within/along the first end member 12, and/or the relative axial position of the second end member 14 within/along the intermediate member 16, may be adjusted along the axis X-X of the strut assembly 10 to provide a relatively large range of length adjustability to the strut assemblies 10 and, thereby the distance and/or orientation between the first and second platforms 120, 130, as shown in FIGS. 10-13 as compared to FIGS. 14-17 for example.

The first and second platforms 120, 130 may be rings or partial rings such that they extend, at least partially, about an opening and/or an axis (and, potentially, at least partially about bone and/or tissue in situ). A plurality of strut assemblies 10 may be coupled to the first and second platforms 120, 130 about the axis and/or opening thereof. For example, as shown in FIGS. 12-19, the plurality of strut assemblies 10 may be positioned and coupled circumferentially to the first and second platforms 120, 130, and each strut assembly 110 may be attached to the first and second platforms 120, 130 via the first and second joints 22, 24, respectively, at differing positions about the axis and/or opening thereof. As such, the strut assemblies 10 may be angled with respect to the axis of first and second platforms 120, 130.

As shown in FIGS. 12-19, the strut assemblies 10 may be arranged and coupled with the first and second platforms 120, 130 in pairs via a joint member 132, and such pairs of strut assemblies 10 (and the joint members 132) may be positioned/spaced circumferentially the first and second platforms 120, 130. Each pair of strut assemblies 10 may be coupled to the first and second platforms 120, 130 in an alternating orientation, as shown in FIGS. 12-19. The strut assemblies 10 of each pair thereof coupled to the first and second platforms 120, 130 may extend to the other platform 120, 130 at opposing axial and/or angular directions. For example, one strut assembly 10 of a pair may extend and couple to the second platform 130 via the first joint 22 from the first platform 120 at a clockwise angle (and position), and the other strut assembly 10 of the pair may extend and couple to the second platform 130 via the second joint 24 from the first platform 120 at a counter-clockwise angle (and position), as shown in FIGS. 12-19.

The intermediate member 16 may be selectively slidably axially adjusted within the cavity of the first end member 12 to provide gross axial length adjustment of the strut assembly 10. The second end member 14 may be selectively threadably axially adjusted within the cavity of the first end member 12 and about/along the threaded rod 18 fixed within the cavity of the intermediate member 16 to provide relatively fine axial length adjustment of the strut assembly 10. In this way, the strut assemblies 10 are able to provide reduction or distraction of the axial distance between portions of the first and second platforms 120, 130 (and the bone or tissue segments coupled thereto) as shown in FIGS. 12-19, over a relatively large adjustment range. This relatively large axial adjustment range of the strut assemblies 10 is provided without the need for the replacement of, or addition to, the strut assemblies 10, which can advantageously free up the surgeon to concentrate on the orthopedic condition and the reduction of the fracture or deformity, as well as reduce needed inventory.

As shown in FIGS. 1-7 and described above, the struts 10 each include a first end member 12, a second end member 14 and an intermediate member 16 that couples and extends between the first end member 12 and the second end member 14. The struts 10 include a threaded rod 18 fixed within the cavity of the intermediate member 16 and threadably coupled within the cavity of the second end member 14. The intermediate member 16 is selectively axially translatably coupled within the cavity of the first end member 12 via a first adjustment mechanism provided at an end portion of the first end member 12, as shown in FIGS. 1-8. As shown in FIGS. 1-7, 10 and 11, the first and second joints or connection mechanisms 22, 24 can be provided at the end portions or free ends of the first end member 12 and the second end member 14, respectively.

As shown in FIGS. 1-6, the first end member 12 comprises a tubular or cylindrical strut body that includes or defines an axially-extending internal cavity from an end portion of the first end member 12 that opposes the first joint 22. As also shown in FIGS. 1-6, the first end member 12 includes an axially extending slot 40 in the strut body that is in communication with the internal cavity thereof. The intermediate member 16 also comprises a tubular or cylindrical strut body that includes or defines an axially-extending internal cavity from an end portion of the intermediate member 16 that is proximate to the first joint 22 (and distal to the second joint 24), as shown in FIGS. 1-6. The intermediate member 16 is axially slidably or translatably received within the internal cavity of the first end member 12, and extends out of/past the end portion of the first end member 12 opposing the first joint 22, as shown in FIGS. 1-6. As shown in FIGS. 1-9, the exterior surface of the strut body of the intermediate member 16 may include a surface texture that increases the friction thereof. For example, the exterior surface of the intermediate member 16 may include axially spaced circumferential grooves/serrations, a friction coating, or any other roughness or friction configuration or material.

As shown in FIGS. 1 and 5-7, the intermediate member 16 may be coupled to (or otherwise include) a radially-extending pin member/portion 48 that is coupled to a portion thereof within the internal cavity of the first end member 12. For example, the pin member 48 may be fixedly coupled to an end portion of the intermediate member 16. The pin member 48 is positioned/received within the slot 40 of the first end member 12 such that the intermediate member 16 is axially slidably received, but rotationally fixed, along/within the internal cavity of the first end member 12. The intermediate member 16 may thereby be axially telescopingly coupled to the first end member 12 but rotationally fixed thereto.

Figure 6:
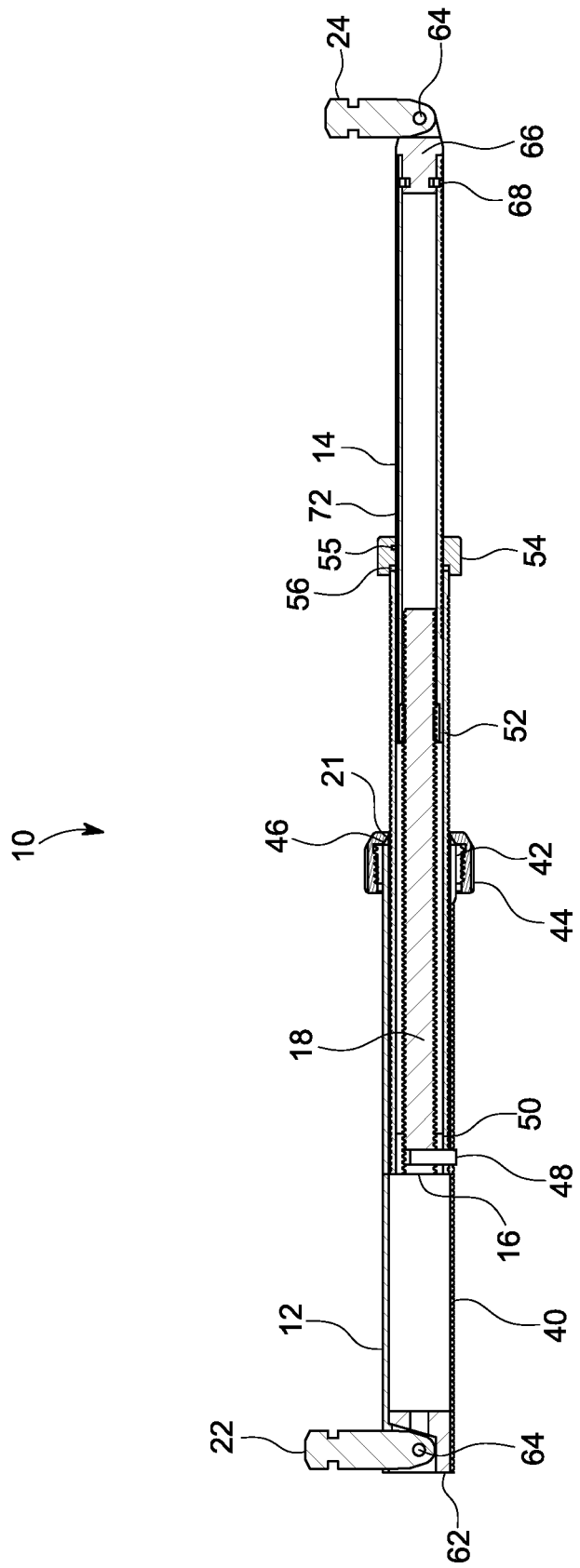
FIG. 6 illustrates a side cross-sectional view of the exemplary adjustable strut assembly of FIG. 1 along axis X-X as indicated in FIG. 5, according to the present disclosure.
Figure 7:
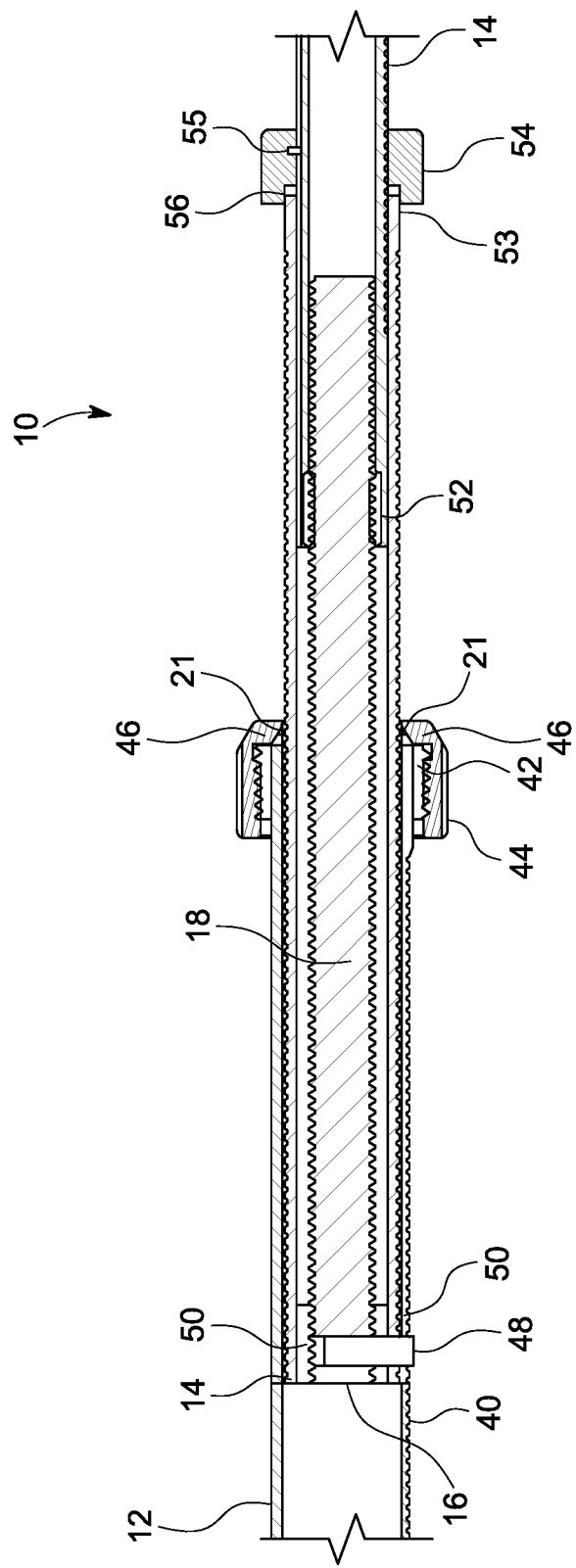
FIG. 7 illustrates an enlarged portion of the cross-sectional view of FIG. 6 of the exemplary adjustable strut assembly of FIG. 1, according to the present disclosure.

As shown in FIGS. 6 and 7, the pin member 48 may also be coupled to the threaded rod 18 to rotatably and axially fixedly couple the threaded rod 18 and the intermediate member 16. For example, the pin member 48 may be fixedly coupled to an end portion of the intermediate member 16. As shown in FIGS. 6 and 7, the intermediate member 16 may include a sleeve, spacer, collar or the like 50 that is positioned within the cavity thereof radially between the threaded rod 18 and the interior surface of the strut body (i.e., the external wall of the cavity). The sleeve may thereby radially space (and potentially center) the threaded rod 18 from the strut body/wall of the cavity, which may allow the second end member 14 to threadably couple and axially and rotatably translate about the threaded rod 18, as explained below. At least an end portion of the second end member 16 can thereby be received within the axial cavity of the intermediate member 16 and positioned radially between the threaded rod 18 and the body portion of the intermediate member 16.

As discussed above, the strut assembly 10 includes a first adjustment mechanism at an end portion, sleeve or bushing 42 of the first end member 12 configured to selectively allow the intermediate member 16 to freely axially translate within the axial cavity of the first end member 12, and to selectively axially fix the intermediate member 16 relative to the first end member 12. As shown in FIGS. 1-8, 10 and 11, the first adjustment mechanism of the strut assembly 10 may include a first collar, ring, knob or rotation member 44 that is threadably rotatably coupled to the end portion 42 of the first end member 12. The end portion 42 of the first end member 12 may be integral with or fixedly coupled to the first end member 12. The end portion 42 may include external threads, and the collar member 44 may include internal threads threadably coupled with the external threads of the end portion 42 such that rotation of the collar member 44 about the second end portion 42 axially translates the first collar 44 along the end portion 42.

Figure 8:
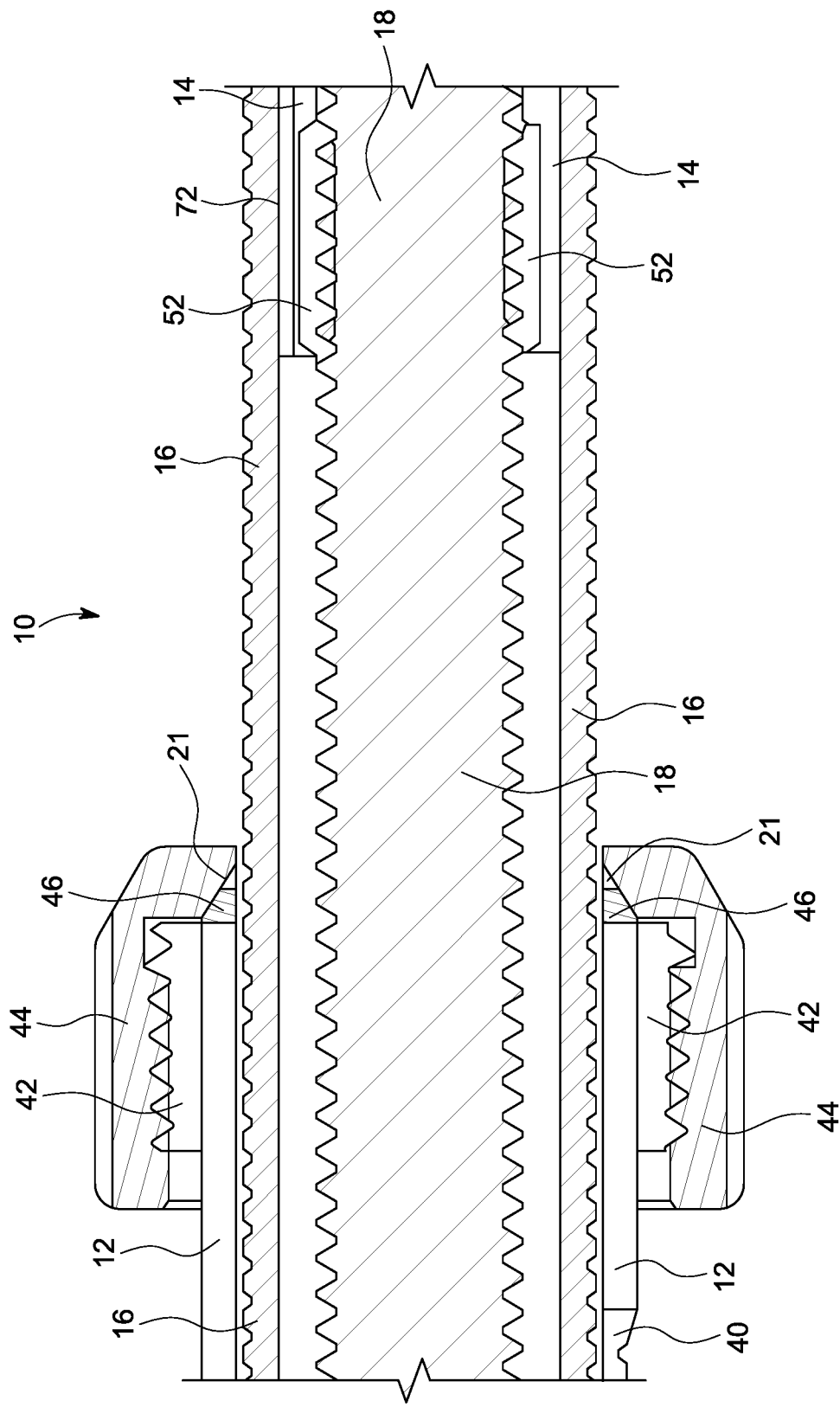
FIG. 8 illustrates an enlarged portion of the cross-sectional view of FIG. 7 of the exemplary adjustable strut assembly of FIG. 1, according to the present disclosure.

As shown in FIGS. 7 and 8, a clamping portion of the collar member 44 is positioned axially past the end portion 42 of the first end member 12 and includes a bearing surface 21. In some embodiments, as shown if FIG. 8, the bearing surface may comprise a tapered surface, such as a surface that is angled towards the exterior surface of the body portion of the intermediate member 16 as it extends axially away from first joint 22 toward the second joint 24.

As also shown in FIGS. 7 and 8, the strut assembly 10 may include a friction or bearing member 46 positioned radially between the exterior surface of the body portion of the intermediate member 16 and the bearing surface 21. In some embodiments, the friction member 46 may comprise a radially deformable member, such as a radially deformable ring member. In some such embodiments, the bearing member 46 may comprises a segmented ring, split ring or like member.

As shown in FIG. 8, the first end member 12, the collar member 44 and the friction member 46 are configured such that axial advancement of the collar member 44 along the end portion 42 of the first end member 12 toward the first joint 22 (e.g., via rotation) causes the bearing surface 21 of the collar member 44 to act against the friction member 46 and force the friction member 46 radially against the exterior surface of the intermediate member 16, and to apply a compressive/friction force thereto (i.e., between the exterior surface of the intermediate member 16 and the friction member 46 (and the bearing surface 21)). Stated differently, axial translation of the collar member 44 along the end portion 42 of the first end member 12 towards the first joint 22 (or the end portion of the first end member 12 coupled to the first joint 22) forces the friction member 46 radially against the exterior surface of the body portion of the intermediate member 16 via the bearing surface 21 to selectively axially fix the intermediate member 16 relative to the first end member 12. Conversely, the first end member 12, the collar member 44 and the friction member 46 are also configured such that axial advancement of the collar member 44 along the end portion 42 of the first end member 12 toward the second end member 14 and/or second joint 24 (e.g., via rotation) causes the bearing surface 21 to translate away form and disengage the friction member 46 and, thereby, allow the friction member 46 to radially move away from or not contact the exterior surface of the intermediate member 16 and/or not apply (or at least reduce) the compressive force applied to the exterior surface of the intermediate member 16 to selectively allow the intermediate member 16 to substantially freely axially translate within the axial cavity of the first end member 12. As such, the axial arrangement of the intermediate member 16 and the first end member 12, and thereby the total axial length of the strut assembly 10, can be easily and quickly grossly selected/configured/adjusted by a user via the collar member 44 (and, potentially, engagement of the first end member and/or intermediate member 16 (or second end member 14, for example), as shown in the arrangements of the strut assemblies 10 of the fixation system 100 in FIGS. 12-16 verse the arrangements of the strut assemblies 10 of the fixation system 100 in FIGS. 16-19, for example.

As discussed above, the strut assembly 10 comprises a second adjustment mechanism configured to selectively rotate the second end member 14 with respect to the intermediate member 16 and the threaded rod 18 to axially translate the second end member 14 relative to the intermediate member 16, and thereby finely adjust the total axial length of the strut assembly 10, as shown in FIGS. 1-7 and 9. As shown in FIGS. 1-7 and 9, the second adjustment mechanism may be provided at an end portion of the intermediate member 16 that is proximate to the second joint 24 (and distal to the first joint 22).

As also discussed above and as shown in FIGS. 6-9, at least a rod engagement portion 52 of the axial cavity of the intermediate member 16 (i.e., of the inner side surface or wall of the strut body portion of the intermediate member 16 forming the internal cavity thereof) may be threadably coupled with the threaded rod. In some embodiments, the engagement portion 52 of the intermediate member 16 may be coupled to the inner side surface or wall of the strut body portion of the intermediate member 16 forming the internal cavity thereof, as shown in FIGS. 6-9. In some other embodiments, the engagement portion 52 of intermediate member 16 maybe integral with or at least a portion of the inner side surface or wall of the strut body portion of the intermediate member 16 forming the internal cavity thereof.

In some embodiments, as shown in FIGS. 6-9, the engagement portion 52 of the intermediate member 16 includes internal threads, and the threaded rod includes external threads threadably coupled with the internal threads of the engagement portion 52 of the intermediate member 16. In some alternative embodiments (not shown), the engagement portion 52 of the intermediate member 16 includes external threads, and the threaded rod includes internal threads threadably coupled with the external threads of the engagement portion 52 of the intermediate member 16.

Figure 9:
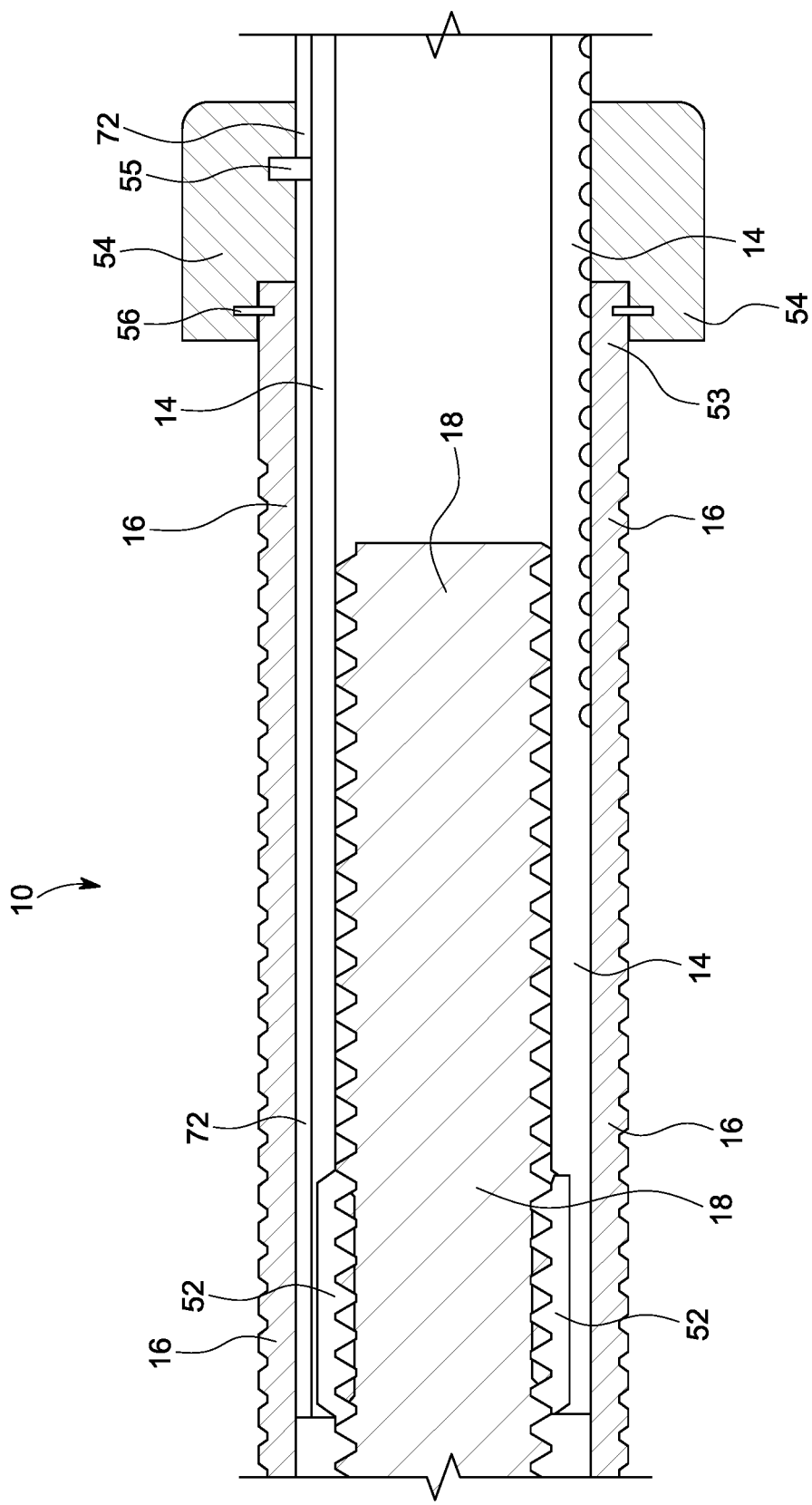
FIG. 9 illustrates another enlarged portion of the cross-sectional view of FIG. 7 of the exemplary adjustable strut assembly of FIG. 1, according to the present disclosure.
Figure 10:
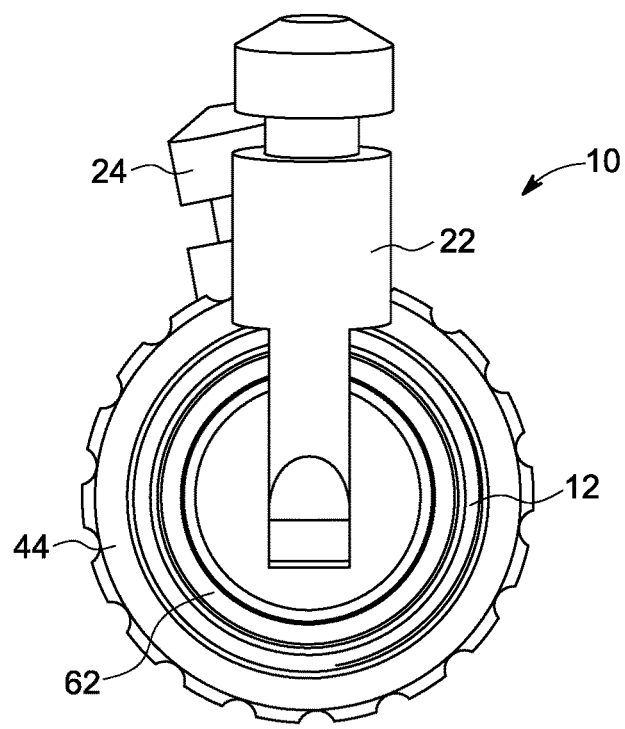
FIG. 10 illustrates a top end view of the exemplary adjustable strut assembly of FIG. 1, according to the present disclosure.
Figure 11:
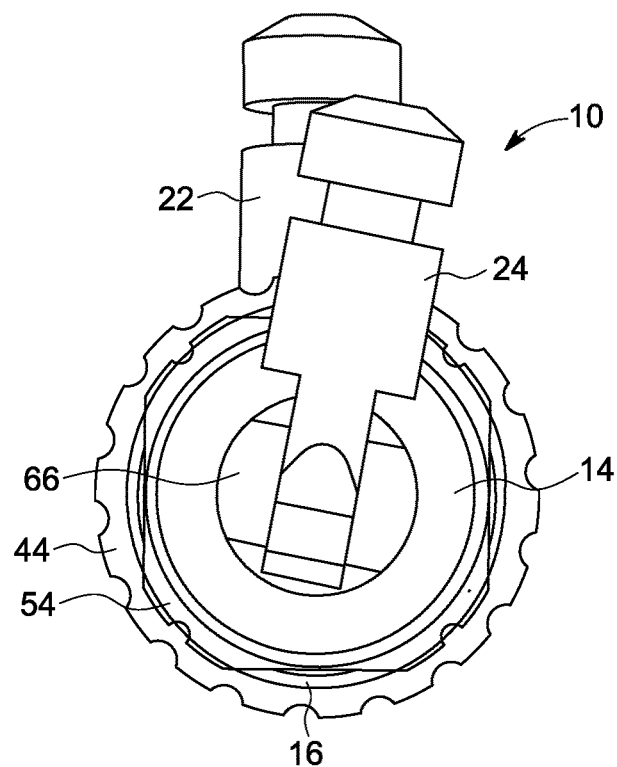
FIG. 11 illustrates a back end view of the exemplary adjustable strut assembly of FIG. 1, according to the present disclosure.
Figure 12:
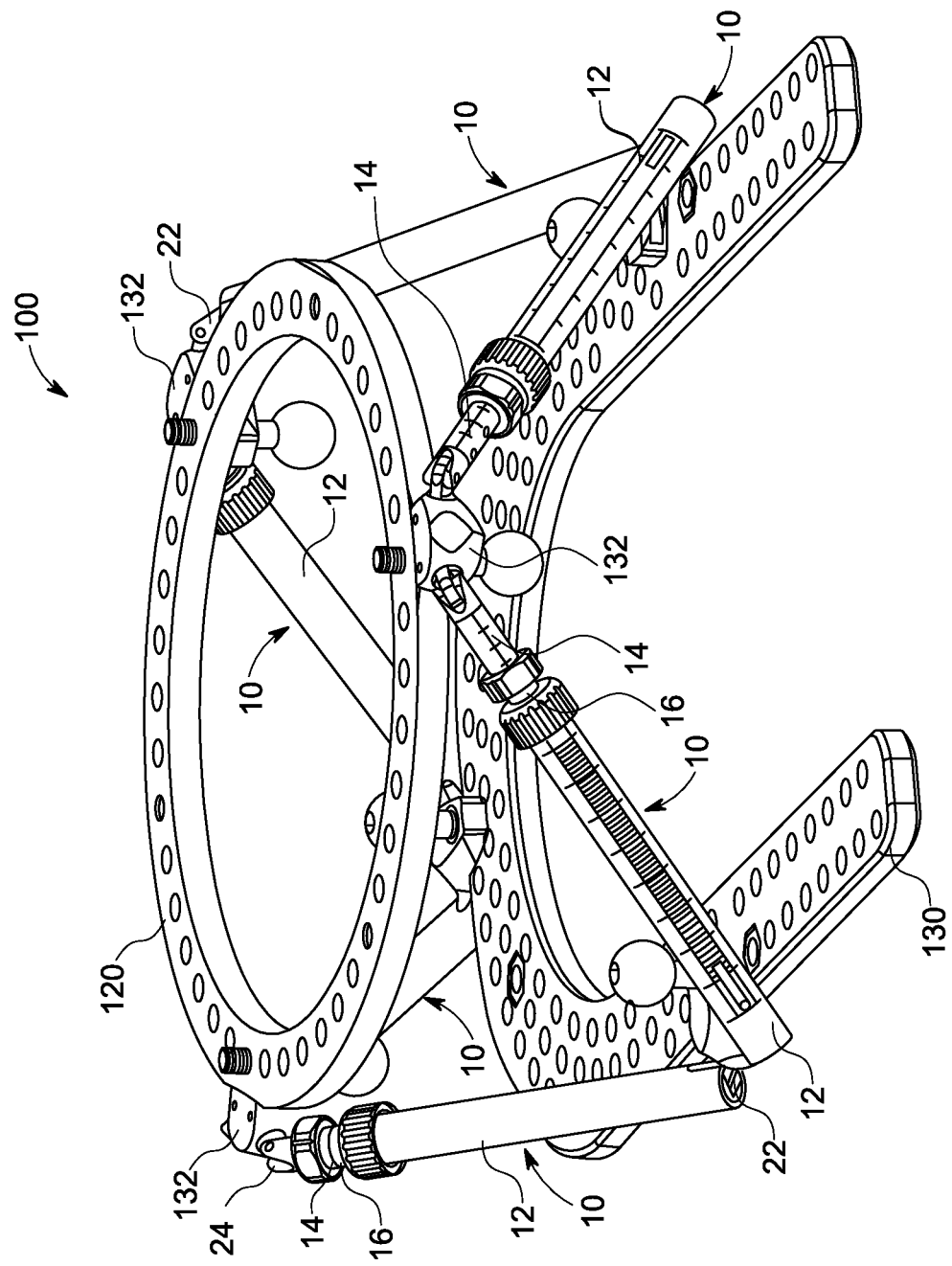
FIG. 12 illustrates a top elevational perspective view of an exemplary external fixation system in a first relatively condensed configuration utilizing the exemplary strut assembly of FIGS. 1-9, according to the present disclosure.
Figure 13:
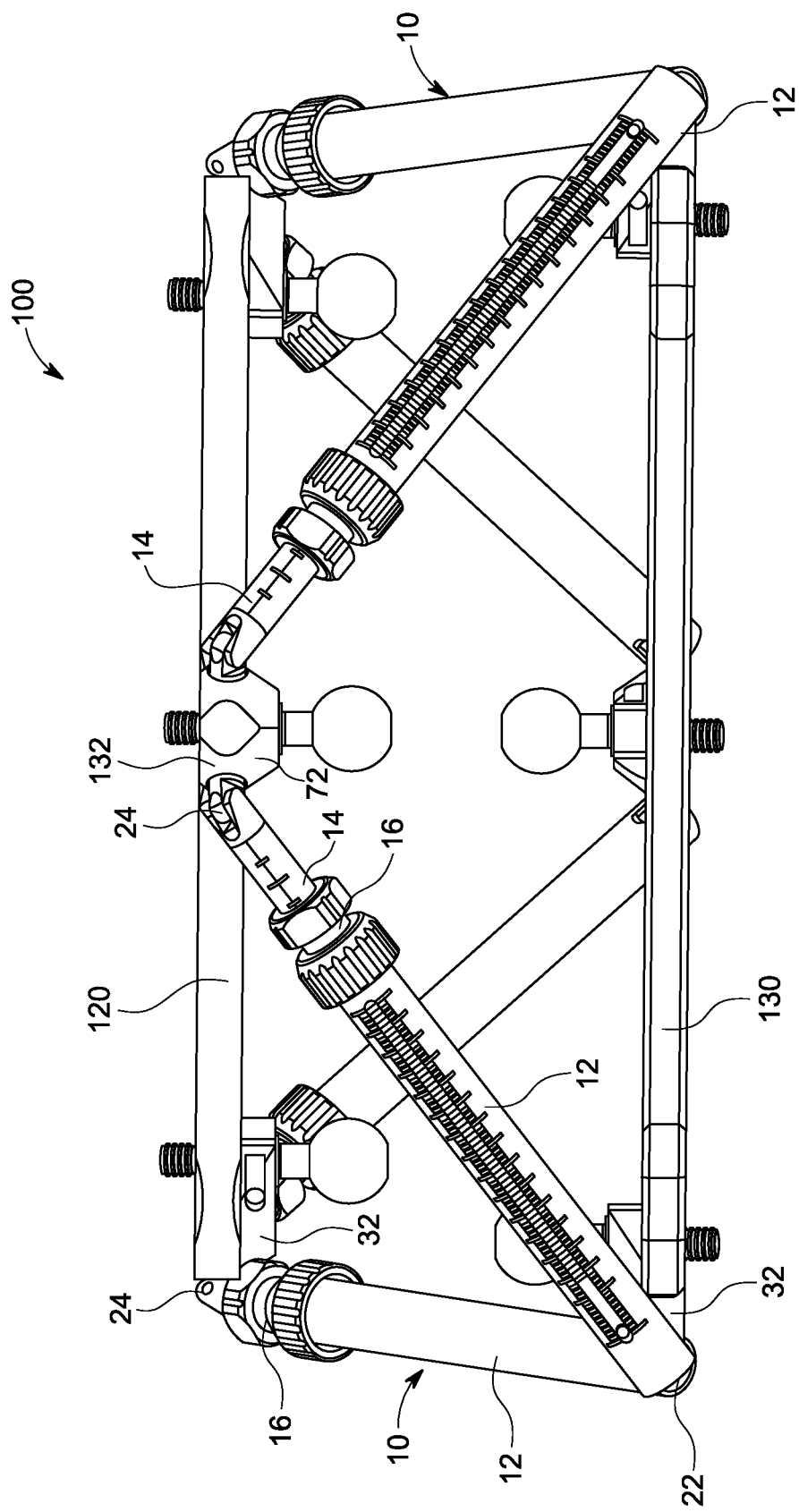
FIG. 13 illustrates a front view of the exemplary external fixation system of FIG. 12, according to the present disclosure.
Figure 14:
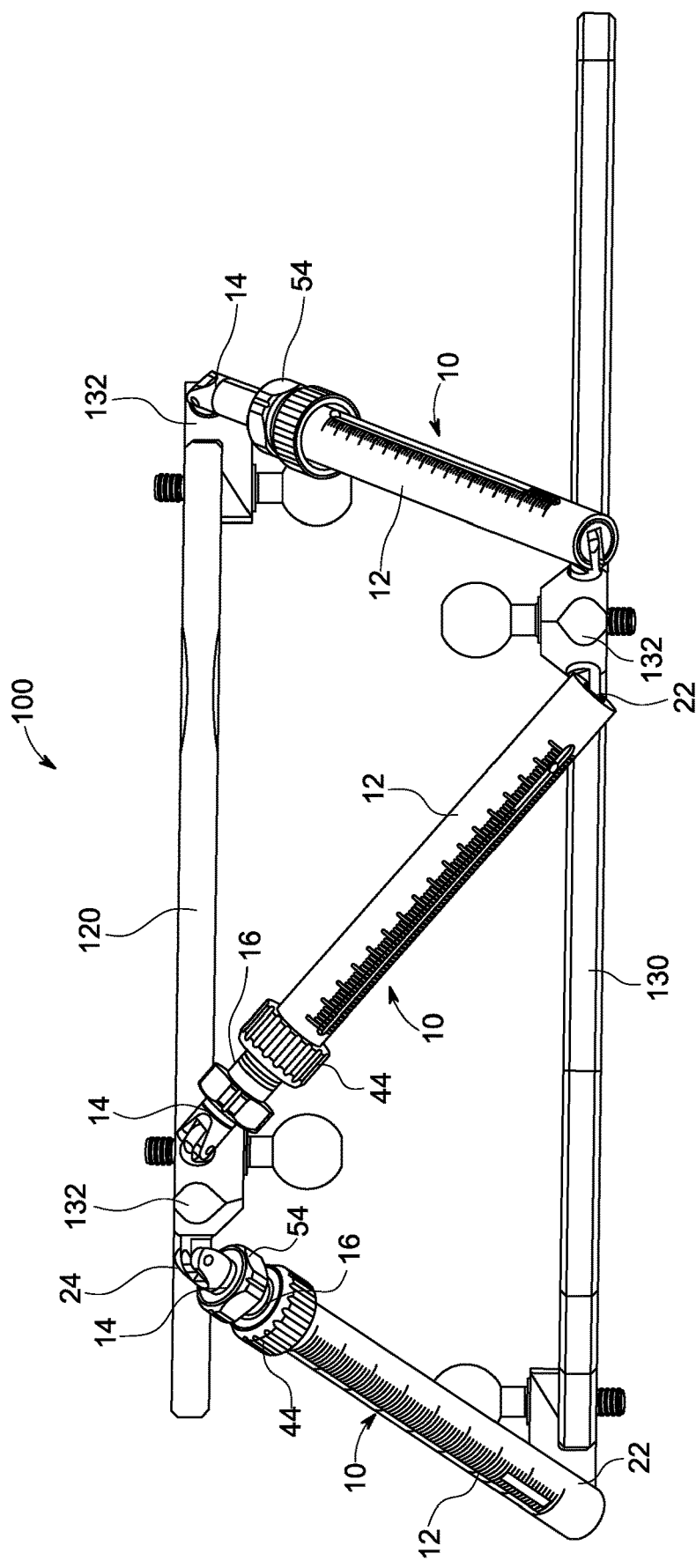
FIG. 14 illustrates a side view of the exemplary external fixation system of FIG. 12, according to the present disclosure.
Figure 15:
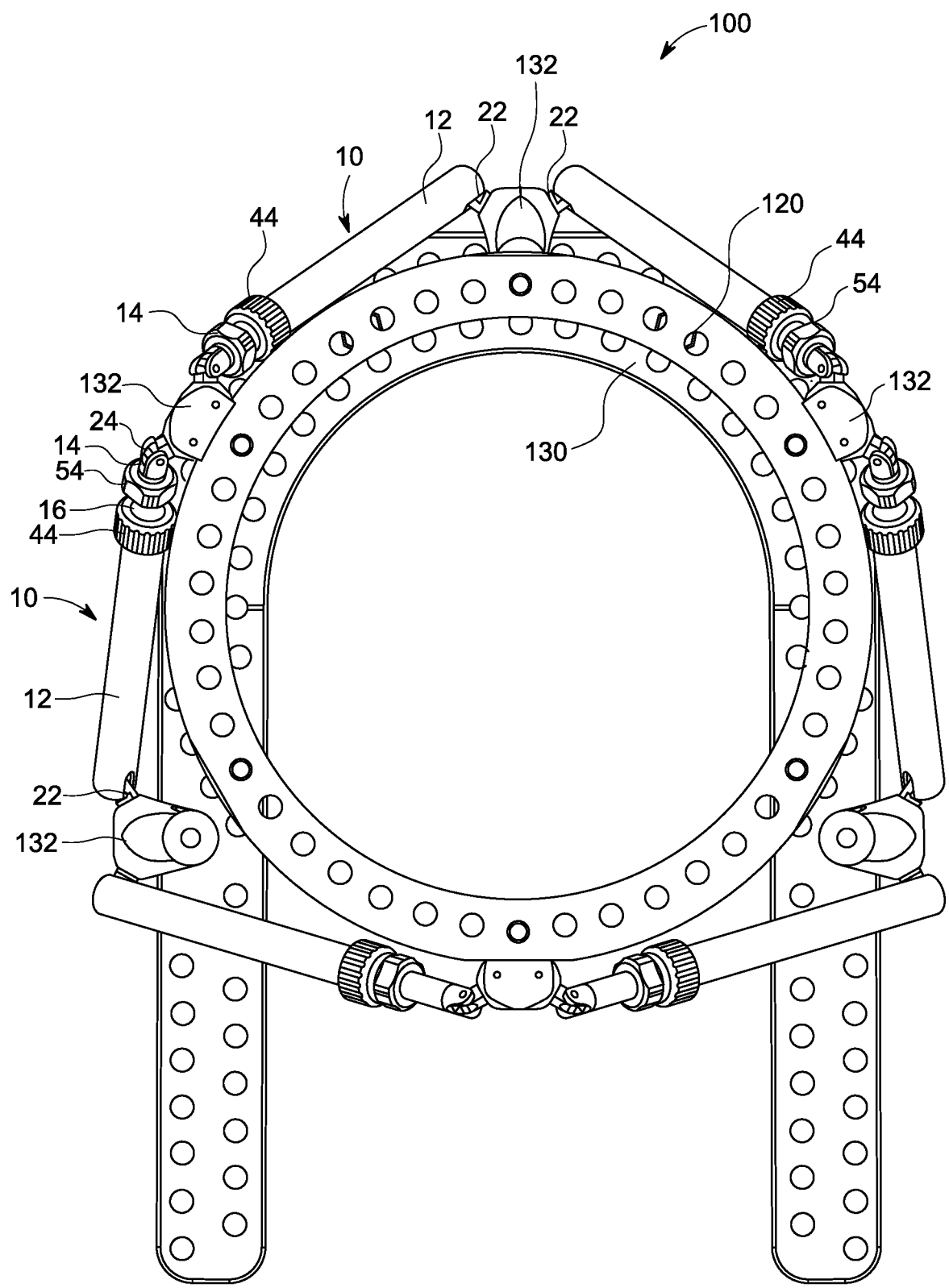
FIG. 15 illustrates a top view of the exemplary external fixation system of FIG. 12, according to the present disclosure.
Figure 16:
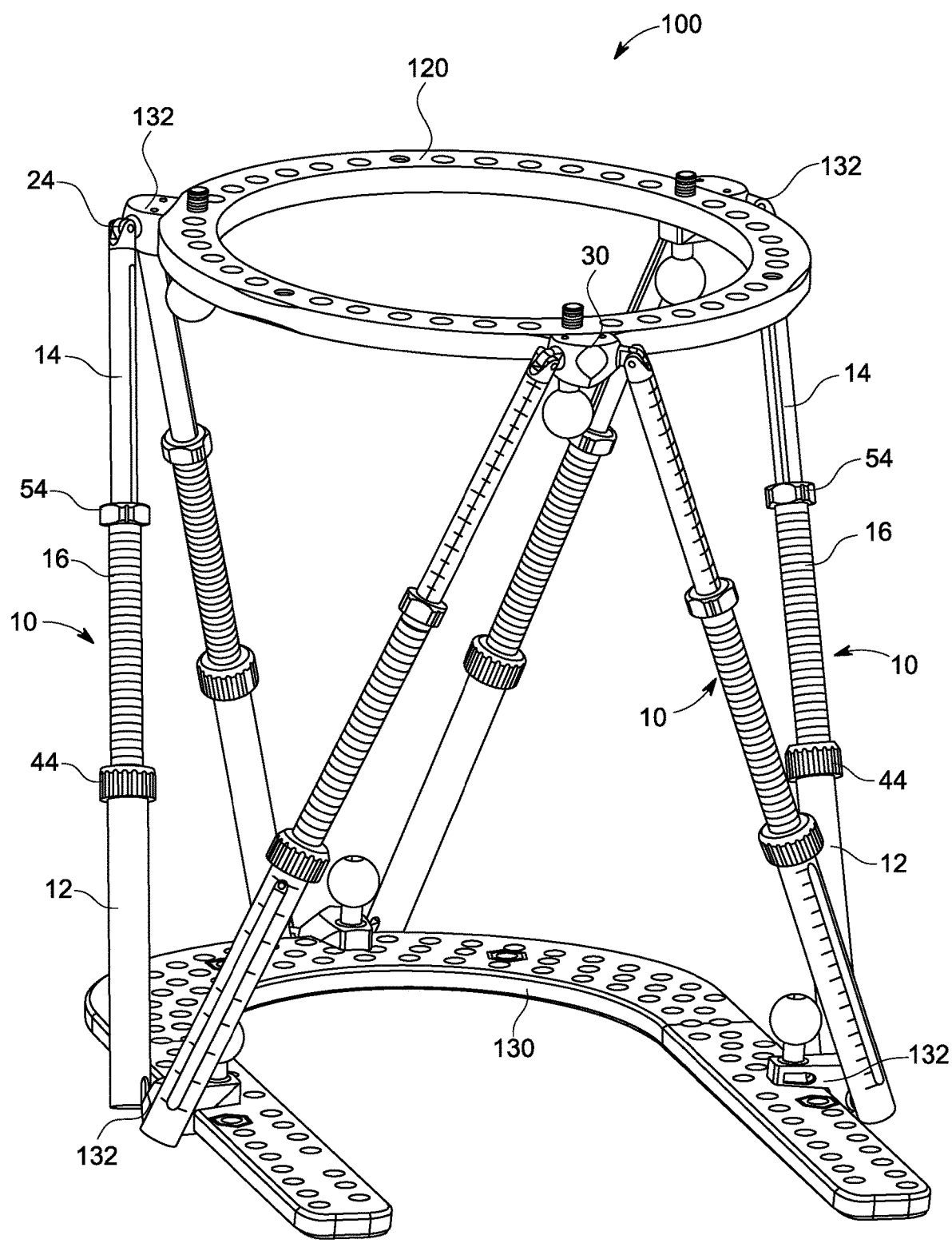
FIG. 16 illustrates a top elevational perspective view of the exemplary external fixation system of FIGS. 12-15 in a second relatively expanded configuration, according to the present disclosure.
Figure 17:
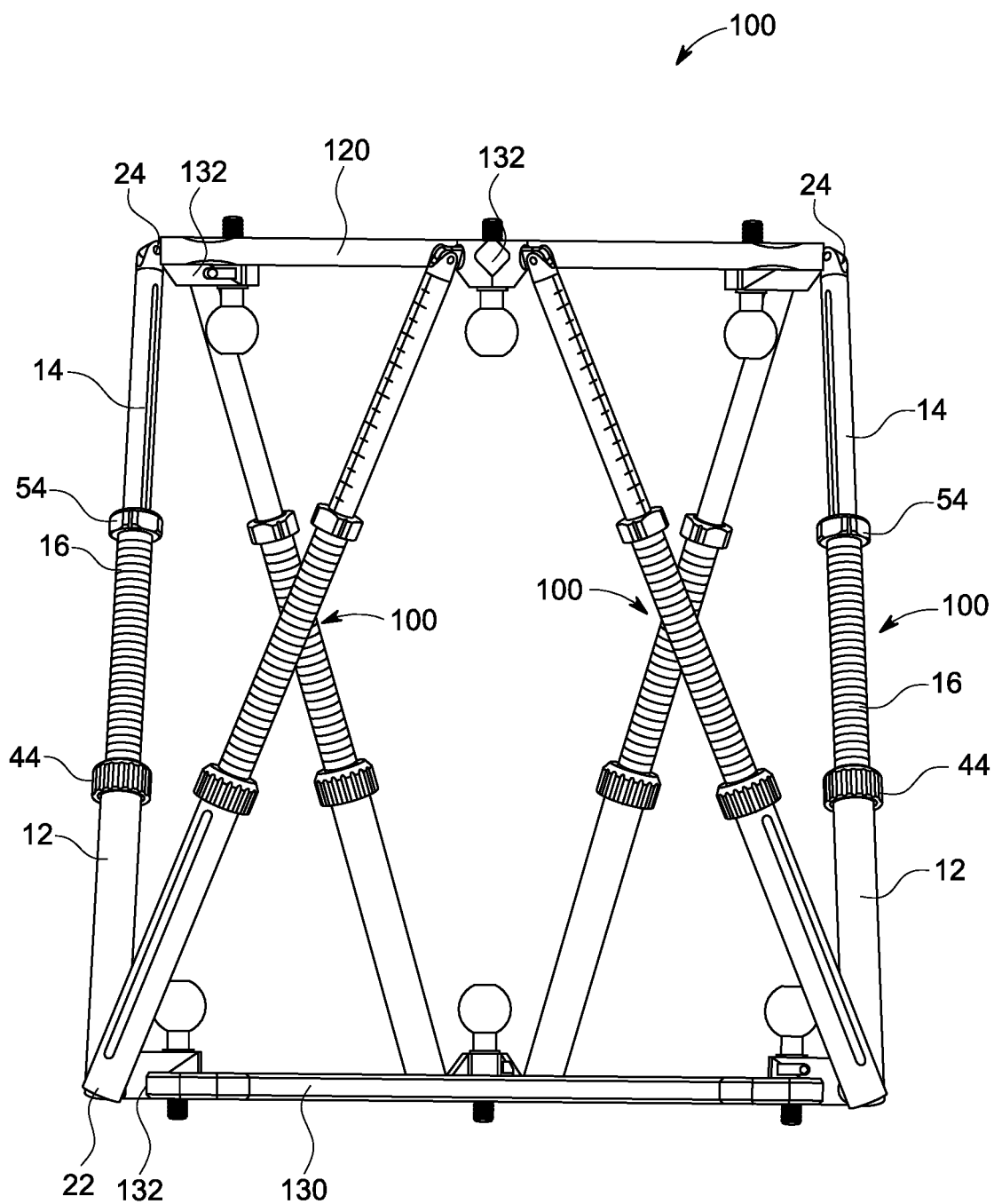
FIG. 17 illustrates a front view of the exemplary external fixation system of FIG. 16, according to the present disclosure.
Figure 18:
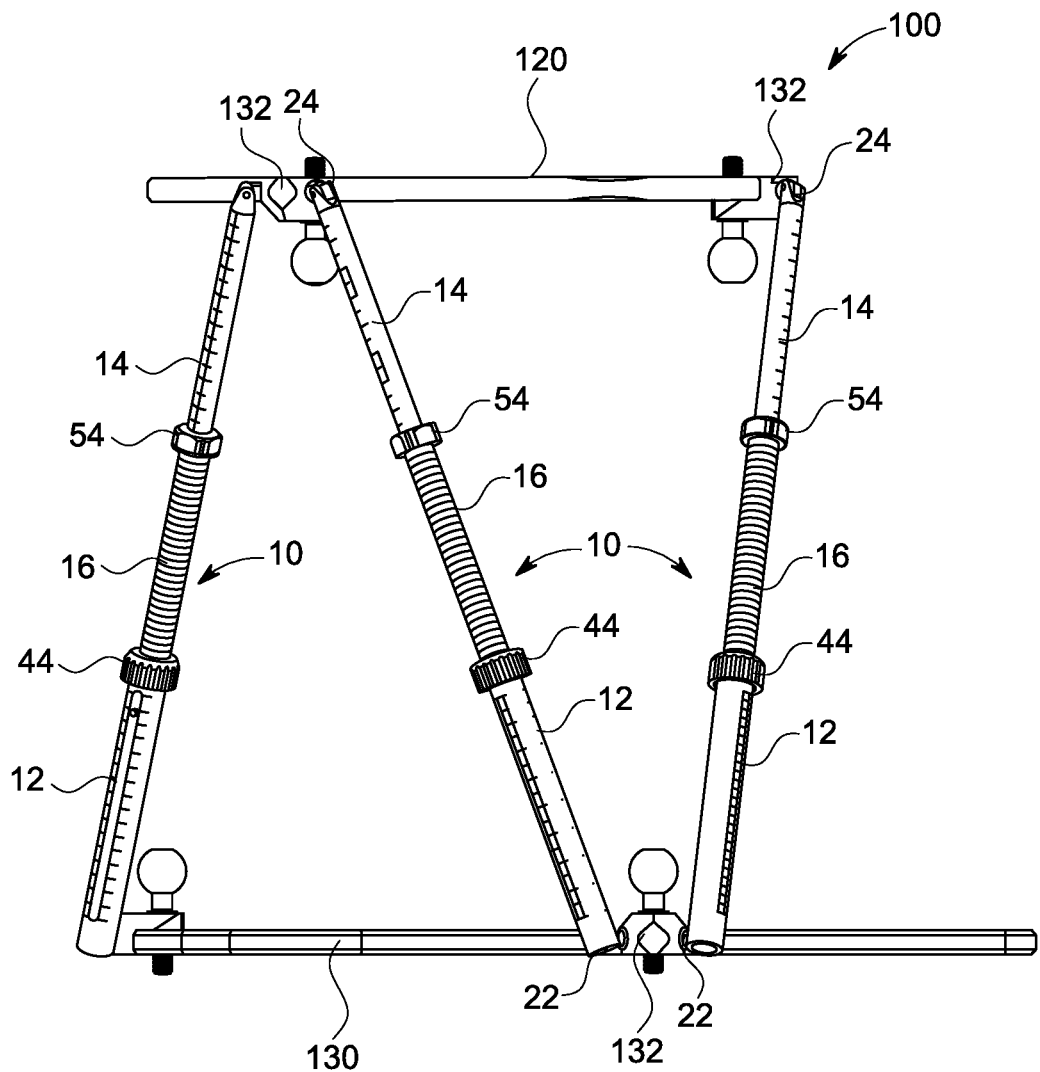
FIG. 18 illustrates a side view of the exemplary external fixation system of FIG. 16, according to the present disclosure.
Figure 19:
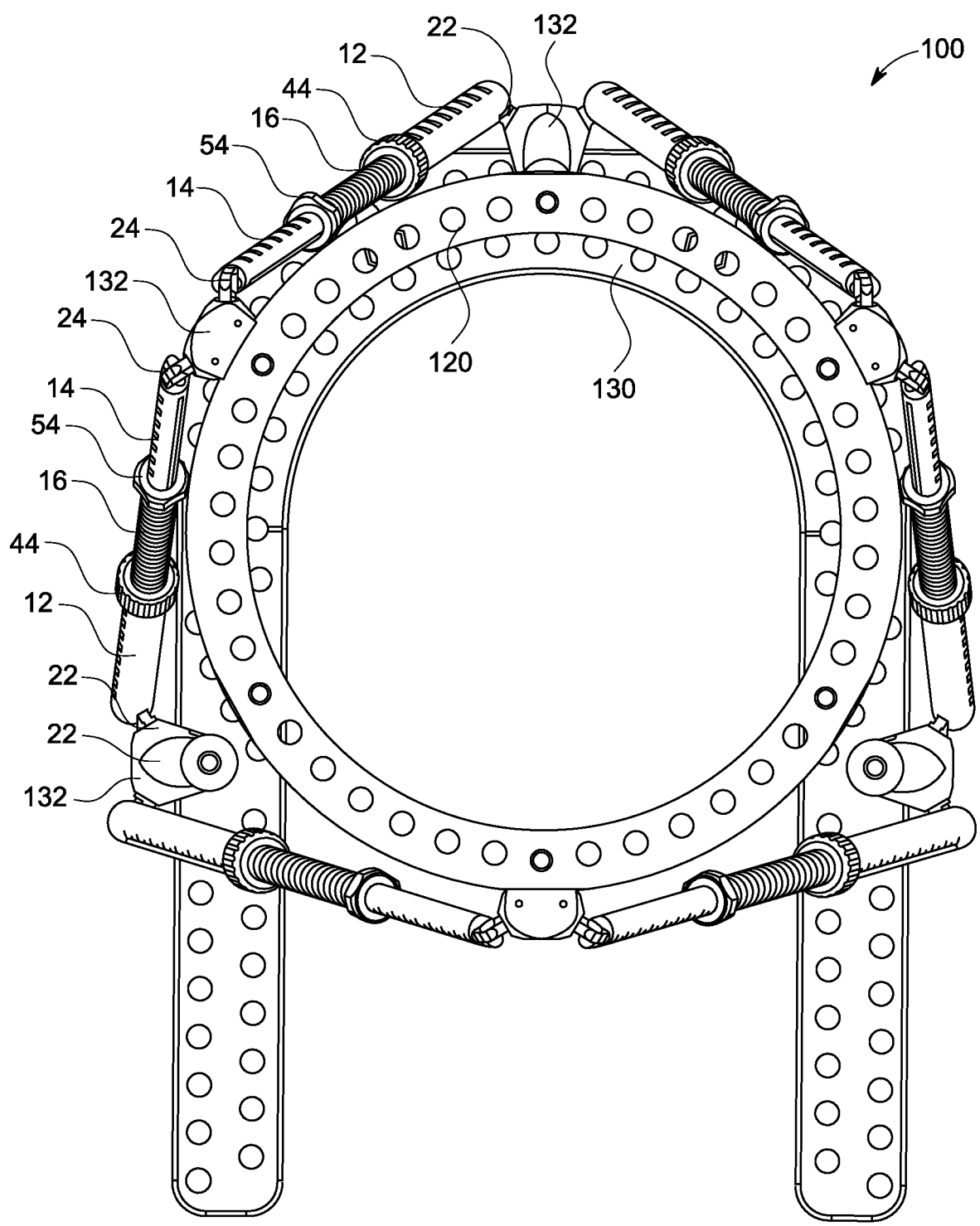
FIG. 19 illustrates a top view of the exemplary external fixation system of FIG. 16, according to the present disclosure.

As shown in FIGS. 1-7 and 9, the second adjustment mechanism comprises a second collar member 54 axially fixed and rotatably coupled to an end portion 53 of the intermediate member 16. As shown in FIGS. 6, 7 and 9, a first portion of the second collar member 54 may extend over and/or about the end portion 53 of the intermediate member 16 and be rotatably coupled and axially fixed thereto. For example, the an inner side of the second collar member 54 and an outer side of the end portion 53 of the intermediate member 16 may include axially aligned circumferential slots or openings and a washer, split ring, O-ring or like member 56 extending therein, as shown in FIGS. 6, 7 and 9. The washer or ring member 56 may thereby allow the first portion of the second collar member 54 to rotate over the end portion 53 of the intermediate member 16 (about the axis X-X), but prevent the second collar member 54 from axially translating over the end portion 53 of the intermediate member 16 (i.e., translating along the axis X-X).

As shown in FIGS. 6, 7 and 9, a second portion of the second collar member 54 may extend over and/or about the second end member 14 and be rotatably fixed thereto (i.e., fixedly coupled thereto). In some embodiments, as shown in FIGS. 6, 7 and 9, the second portion of the second collar member 54 may be coupled to (or otherwise include) a radially-extending pin member/portion 55. As shown in FIGS. 2, 3 and 6-9, the outer surface of the strut body portion of the second end member 14 may include an axially-extending slot 72 that accepts or receives the pin member 55 therein. The pin member 55 and the slot 72 are configured such that the pin member 55 is able to axially-translate through/along the axial length of the slot 72. The pin member 55 (extending in the pin member 55 and the slot 72 of the second end member) thereby rotatably fixes or fixedly couples the second collar member 54 and the second end member together, but allows the second end member 14 to axially-translate with respect to the pin member 55 and, thereby, the intermediate member 16.

Rotation of the second collar member 54 over and/or about the second end member 14 (i.e., about the axis X-X) thereby causes the second end member 14 to rotate within the cavity of the intermediate member 16 and about the threaded rod 18 (i.e., axially rotate within the cavity with respect to the intermediate member 16 and the threaded rod 18). As the engagement portion 52 of the second member 14 and the threaded rod 18 are threadably coupled, rotation of the second collar member 54 rotates the second end member 14 with respect to the threaded rod 18, which thereby axially translates the second end member 14 relative to the intermediate member 16. As such, the axial arrangement of the intermediate member 16 and the second end member 14, and thereby the total axial length of the strut assembly 10, can be easily and quickly finely selected/configured/adjusted by a user via the second collar member 54 (i.e., via rotation of the second collar member 54 about the axis X-X in a particular angular direction), as shown in the arrangements of the strut assemblies 10 of the fixation system 100 in FIGS. 12-16 verse the arrangements of the strut assemblies 10 of the fixation system 100 in FIGS. 16-19, for example.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A strut assembly for an external fixation system, comprising:
   an elongate first end member comprising a first end portion, a second end portion, and a first axial cavity extending from the second end portion;
   an elongate intermediate member comprising a third end portion, a fourth end portion, a second axial cavity extending from the third end portion, and a threaded rod rotatably and axially fixedly coupled within the second axial cavity, the intermediate member being rotatably fixed and axially translatably within the first axial cavity of the first end member and extending therefrom through the second end portion;
   an elongate second end member comprising a fifth end portion, a sixth end portion, and a third axial cavity extending from the fifth end portion, at least the fifth end portion of the second end member being received within the second axial cavity of the intermediate member and the third axial cavity being threadably coupled with the threaded rod of the intermediate member, the second end member extending from the second axial cavity through the fourth end portion;
   a first adjustment mechanism at the second end portion of the first end member configured to selectively allow the intermediate member to freely axially translate within the first axial cavity and to selectively axially fix the intermediate member relative to the first end member; and
   a second adjustment mechanism at the fourth free end portion of the intermediate member configured to selectively rotate the second end member with respect to the intermediate member and the threaded rod to axially translate the second end member relative to the intermediate member.

2. The strut assembly according to claim 1, wherein the first end portion of the first end member includes a first joint configured to couple to a first external fixation platform.

3. The strut assembly according to claim 1, wherein the sixth end portion of the second end member includes a second joint configured to couple to a second external fixation platform.

4. The strut assembly according to claim 1, wherein a body portion of the first end member includes an axial-extending slot, and wherein the intermediate member is rotatably fixed and axially translatably within the first axial cavity of the first end member via a radially extending first pin that is coupled to the intermediate member and is received within the slot of the first end member.

5. The strut assembly according to claim 4, wherein the first pin is coupled to the third end portion of the intermediate member.

6. The strut assembly according to claim 4, wherein the first pin is further coupled to the threaded rod to rotatably and axially fixedly couple the threaded rod and the intermediate member.

7. The strut assembly according to claim 6, wherein the first pin is coupled to an end portion of the threaded rod.

8. The strut assembly according to claim 1, wherein at least the fifth end portion of the second end member that is received within the second axial cavity of the intermediate member is positioned radially between the threaded rod and a body portion of the intermediate member.

9. The strut assembly according to claim 1, wherein the third axial cavity of the intermediate member comprises internal threads and the threaded rod comprises external threads threadably coupled with the internal threads of the third axial cavity.

10. The strut assembly according to claim 1, wherein the second end portion of the first end member comprises external threads, wherein the first adjustment mechanism comprises an internally threaded first collar member threadably coupled with the external threads of the second end portion, and wherein rotation of the first collar member about the second end portion axially translates the first collar along the second end portion.

11. The strut assembly according to claim 10, wherein a clamping portion of the first collar member is positioned axially past the second end portion of the first end member and includes a tapered bearing surface, and wherein the first adjustment mechanism further comprises friction member positioned radially between an exterior surface of a body portion of the intermediate member and the bearing surface.

12. The strut assembly according to claim 11, wherein axial translation of the first collar along the second end portion towards the first end portion forces the friction member radially against the exterior surface of a body portion of the intermediate member via the bearing surface to selectively axially fix the intermediate member relative to the first end member.

13. The strut assembly according to claim 12, wherein the bearing surface comprises a surface that is angled towards the exterior surface of the body portion of the intermediate member as it extends axially away from the second end portion.

14. The strut assembly according to claim 12, wherein the friction member comprises a deformable ring member.

15. The strut assembly according to claim 14, wherein the deformable ring member comprises a segmented ring or a split ring.

16. The strut assembly according to claim 12, wherein the exterior surface of the body portion of the intermediate member comprises a friction-enhancing surface texture.

17. The strut assembly according to claim 1, wherein the second adjustment mechanism comprises a second collar member axially fixed and rotatably coupled to the fourth end portion of the intermediate member.

18. The strut assembly according to claim 17, wherein a body portion of second end member includes an axial-extending slot, and wherein the second collar member is rotatably fixed to the second end member via a radially extending second pin that is coupled to the second collar member and is received within the slot of the second end member such that rotation of the second collar member about the fourth end portion axially translates the second end member relative to the intermediate member.

19. An external bone and/or tissue fixation system, comprising:
a first platform;
a second platform; and
a plurality of struts extending between the first and second platforms,
wherein at least one of the plurality of struts comprises the strut assembly according to claim 1.

20. The external bone and/or tissue fixation system according to claim 19, wherein a plurality of the plurality of struts comprise the strut assembly of claim 1.

21. The external bone and/or tissue fixation system according to claim 19, wherein each of the plurality of struts comprises the strut assembly of claim 1.

22. The external bone and/or tissue fixation system according to claim 19, wherein the plurality of struts comprises six struts.

23. The strut assembly according to claim 22, wherein the second adjustment mechanism comprises a second collar member axially fixed and rotatably coupled to the fourth end portion of the intermediate member.

24. The strut assembly according to claim 23, wherein a body portion of second end member includes an axial-extending slot, and wherein the second collar member is rotatably fixed to the second end member via a radially extending second pin that is coupled to the second collar member and is received within the slot of the second end member such that rotation of the second collar member about the fourth end portion axially translates the second end member relative to the intermediate member.

25. The external bone and/or tissue fixation system according to claim 19, wherein the first platform is configured to be coupled to a first bone and/or tissue of a patient, and the second platform is configured to be coupled to a second bone and/or tissue of a patient.

26. The strut assembly according to claim 19, wherein the first end portion of the first end member includes a first joint configured to couple to a first external fixation platform.

27. The strut assembly according to claim 19, wherein the sixth end portion of the second end member includes a second joint configured to couple to a second external fixation platform.

28. The strut assembly according to claim 19, wherein a body portion of the first end member includes an axial-extending slot, and wherein the intermediate member is rotatably fixed and axially translatably within the first axial cavity of the first end member via a radially extending first pin that is coupled to the intermediate member and is received within the slot of the first end member.

29. The strut assembly according to claim 28, wherein the first pin is coupled to the third end portion of the intermediate member.

30. The strut assembly according to claim 28, wherein the first pin is further coupled to the threaded rod to rotatably and axially fixedly couple the threaded rod and the intermediate member.

31. The strut assembly according to claim 30, wherein the first pin is coupled to an end portion of the threaded rod.

32. The strut assembly according to claim 19, wherein at least the fifth end portion of the second end member received within the second axial cavity of the intermediate member is positioned radially between the threaded rod and a body portion of the intermediate member.

33. The strut assembly according to claim 19, wherein the third axial cavity of the intermediate member comprises internal threads and the threaded rod comprises external threads threadably coupled with the internal threads of the third axial cavity.

34. The strut assembly according to claim 19, wherein the second end portion of the first end member comprises external threads, wherein the first adjustment mechanism comprises an internally threaded first collar member threadably coupled with the external threads of the second end portion, and wherein rotation of the first collar member about the second end portion axially translates the first collar along the second end portion.

35. The strut assembly according to claim 34, wherein a clamping portion of the first collar member is positioned axially past the second end portion of the first end member and includes a tapered bearing surface, and wherein the first adjustment mechanism further comprises friction member positioned radially between an exterior surface of a body portion of the intermediate member and the bearing surface.

36. The strut assembly according to claim 35, wherein axial translation of the first collar along the second end portion towards the first end portion forces the friction member radially against the exterior surface of a body portion of the intermediate member via the bearing surface to selectively axially fix the intermediate member relative to the first end member.

37. The strut assembly according to claim 36, wherein the bearing surface comprises a surface that is angled towards the exterior surface of the body portion of the intermediate member as it extends axially away from the second end portion.

38. The strut assembly according to claim 37, wherein the friction member comprises a deformable ring member.

39. The strut assembly according to claim 38, wherein the deformable ring member comprises a segmented ring or a split ring.

40. The strut assembly according to claim 36, wherein the exterior surface of the body portion of the intermediate member comprises a friction-enhancing surface texture.

\* \* \* \* \*